US007933430B2

(12) United States Patent  (10) Patent No.: US 7,933,430 B2
Schweitzer  (45) Date of Patent: Apr. 26, 2011

(54) METHOD AND APPARATUS FOR SPECTRAL MIXTURE RESOLUTION (75) Inventor: Robert Schweitzer, Pittsburgh, PA (US)

(73) Assignee: ChemImage Corporation, Pittsburgh, PA (US)

(*) Notice: Subject to any disclaimer, the term of this patent is extended or adjusted under 35 U.S.C. 154(b) by 862 days.

(21) Appl. No.: 11/918,490

(22) PCT Filed: Apr. 15, 2005

(86) PCT No.: PCT/US2005/013036
§ 371 (c)(1),
(2), (4) Date: Oct. 15, 2007

(87) PCT Pub. No.: WO2006/112832
PCT Pub. Date: Oct. 26, 2006

(65) Prior Publication Data
US 2009/0043514 A1   Feb. 12, 2009

(51) Int. Cl.
G06K 9/00 (2006.01)
G01J 3/44 (2006.01)

(52) U.S. Cl. .......... 382/100; 382/103; 382/107; 702/23; 702/27; 702/30; 702/76; 702/196; 356/301; 356/417; 356/318

(58) Field of Classification Search .................. 702/26, 702/23, 27, 30, 76, 194, 196; 382/100, 103, 382/107; 356/417, 301, 318, 317
See application file for complete search history.

(56) References Cited

U.S. PATENT DOCUMENTS

| 4,660,151 A | * | 4/1987 | Chipman et al. ............ 702/23 |
| 4,701,838 A | | 10/1987 | Swinkels et al. |
| 4,766,551 A | | 8/1988 | Begley |
| 4,885,697 A | | 12/1989 | Hubner |
| 5,121,337 A | | 6/1992 | Brown |
| 5,121,338 A | | 6/1992 | Lodder |

(Continued)

FOREIGN PATENT DOCUMENTS

| EP | 0807809 A | 11/1997 |
| WO | 8501348 A | 3/1985 |

OTHER PUBLICATIONS

Mario R. Caetano, et al.; Evaluation of the Importance of Non-Linear Spectral Mixing in Coniferous Forests; Sep. 1998; SPIE vol. 3499; pp. 257-269.

(Continued)

Primary Examiner — Wesley Tucker
Assistant Examiner — Nancy Bitar
(74) Attorney, Agent, or Firm — Duane Morris (57) ABSTRACT The spectral method for determining the concentrations of a substance in a mixture of any number of substances is defined by a chemical image having a plurality of pixels (520). The method includes steps of providing a spectrum for each of the n number of substances in the mixture (530), and obtaining the spectrum for one of the plurality of pixels, and calculating a plurality of estimated concentrations of each substance in the mixture as a function of the spectrum for each substance and the spectrum for the pixel, and calculating a deviation value for each of the plurality of estimated concentrations as a function of the spectrum of each of the number of substances in the mixture, and selecting the estimated concentration with the lowest deviation factor as a most likely concentration of each substance in the mixture (550).

48 Claims, 9 Drawing Sheets

U.S. PATENT DOCUMENTS

| | | | |
|---|---|---|---|
| 5,124,932 | A | 6/1992 | Lodder |
| 5,311,445 | A | 5/1994 | White |
| 5,481,476 | A | 1/1996 | Windig |
| 5,606,164 | A | 2/1997 | Price et al. |
| 5,610,836 | A | 3/1997 | Alsmeyer et al. |
| 5,684,580 | A * | 11/1997 | Cooper et al. ............... 356/301 |
| 5,710,713 | A | 1/1998 | Wright et al. |
| 5,822,219 | A * | 10/1998 | Chen et al. .................... 702/27 |
| 6,341,257 | B1 * | 1/2002 | Haaland ......................... 702/27 |
| 6,490,530 | B1 | 12/2002 | Wyatt |
| 6,549,861 | B1 | 4/2003 | Mark et al. |
| 6,584,413 | B1 * | 6/2003 | Keenan et al. ................ 702/28 |
| 6,675,106 | B1 * | 1/2004 | Keenan et al. ................ 702/28 |
| 6,959,248 | B2 | 10/2005 | Gard et al. |

OTHER PUBLICATIONS

Remote Sensing for Agriculture, Ecosystems, and Hydrology; Sep. 22-24, 1998; SPIE vol. 3499.

G.T. Rasmussen, et al.; Library Retrieval of Infrared Spectra Based on Detailed Intensity Information; Nov. 4, 1979; Applied Spectroscopy; vol. 33, pp. 371-376.

European Patent Office, Extended European Search Report for Application No. 06735747.5, mailed Nov. 28, 2008.

Jean Guilment, et al.; Infrared Chemical Micro-Imaging Assisted by Interactive Self Modeling Multivariate analysis; Nov. 3, 1994; Applied Spectroscopy; vol. 48, pp. 320-326.

Edmund R. Malinowski; Factor Analysis in Chemistry; 1991; second edition; published by John Wiley & Sons, Inc.

William H. Press, et al.; Numerical Recipes in C, the Art of Scientific Computing; Second Edition; originally published 1992—latest publication date 2002; published by Press Syndicate of the University of Cambridge.

* cited by examiner

Fig. 3A
Baking Soda

Fig. 3B
Corn Starch

Fig. 3C
Microcrystalline Cellulose

Fig. 3D
Cane Sugar

Fig. 4
All Mixture Spectra

METHOD AND APPARATUS FOR SPECTRAL MIXTURE RESOLUTION

The instant disclosure relates to application Ser. No. 10/812,233, filed Mar. 29, 2004, the specification of which is incorporated herein in its entirety for background information.

It is becoming increasingly important and urgent to rapidly and accurately identify toxic materials or pathogens with a high degree of reliability, particularly when the toxins/pathogens may be purposefully or inadvertently mixed with other materials. In uncontrolled environments, such as the atmosphere, a wide variety of airborne organic particles from humans, plants and animals occur naturally. Many of these naturally occurring organic particles appear similar to some toxins and pathogens even at a genetic level. It is important to be able to distinguish between these organic particles and the toxins/pathogens.

In cases where toxins and/or pathogens are purposely used to inflict harm or damage, they are typically mixed with so-called "masking agents" to conceal their identity. These masking agents are used to trick various detection methods and apparatus to overlook or be unable to distinguish the toxins/pathogens mixed therewith. This is a recurring concern for homeland security where the malicious use of toxins and/or infectious pathogens may disrupt the nation's air, water and/or food supplies. Additionally, certain businesses and industries could also benefit from the rapid and accurate identification of the components of mixtures and materials. One such industry that comes to mind is the drug manufacturing industry, where the identification of mixture composition could aid in preventing the alteration of prescription and non-prescription drugs.

One known method for identifying materials and organic substances contained within a mixture is to measure the absorbance, transmission, reflectance or emission of each component of the given mixture as a function of the wavelength or frequency of the illuminating or scattered light transmitted through the mixture. This, of course, requires that the mixture be separable into its component parts. Such measurements as a function of wavelength or frequency produce a plot that is generally referred to as a spectrum. The spectra of the components of a given mixture, material or object, i.e., a sample spectra, can be identified by comparing the sample spectra to set a reference spectra that have been individually collected for a set of known elements or materials. The set of reference spectra are typically referred to as a spectral library, and the process of comparing the sample spectra to the spectral library is generally termed a spectral library search. Spectral library searches have been described in the literature for many years, and are widely used today. Spectral library searches using infrared (approximately 750 nm to 100 μm wavelength), Raman, fluorescence or near infrared (approximately 750 nm to 2500 nm wavelength) transmissions are well suited to identify many materials due to the rich set of detailed features these spectroscopy techniques generally produce. The above-identified spectroscopy techniques produce a rich fingerprint of the various pure entities that are currently used to identify them in mixtures which are separable into its component parts via spectral library search.

Conventional library searches generally cannot even determine the composition of mixtures—they may be used if the user has a pure target spectrum (of a pure unknown) and would like to search against the library to identify the unknown compound.

SUMMARY

In one embodiment, the disclosure relates to a method for determining concentration of a substance in a mixture of n substances defined by a chemical image having a plurality of pixels, the method comprising: (a) providing a spectrum for each of the n substances in the mixture; (b) obtaining a spectrum for one of the plurality of pixels, the spectrum defining the pixel as a function of intensity and wavelength; (c) calculating an estimated concentration for each substance in the mixture as a function of the spectrum for each substance and the pixel spectrum; (d) calculating an estimated pure spectrum for each substance as a function of the estimated concentration for each substance and the pixel spectrum; (e) calculating a deviation value as a function of the estimated pure spectrum and the spectrum provided in step (b); (f) repeating steps (c)-(e) $2^n-1$ times with different combination of n substances to determine m deviation values; and (g) selecting the lowest deviation value from among m deviation values as the most-likely concentration for each substance in the mixture.

In another embodiment, the disclosure relates to a method for determining concentration of a substance in a mixture of n substances defined by a chemical image having a plurality of pixels, the method comprising: (i) providing a spectrum for each of the n substances in the mixture; (ii) obtaining a spectrum for one of the plurality of pixels; (iii) calculating a plurality of estimated concentrations for each substance in the mixture as a function of the spectrum for each substance and the pixel spectrum; (iv) calculating a deviation value for each of the plurality of estimated concentrations as a function of the estimated concentration and the spectrum for each of the n substances; and (v) selecting the estimated concentration with the lowest deviation value as a most-likely concentration of each substance in the mixture.

In still another embodiment, the disclosure relates to an apparatus for determining concentration of a substance in a mixture of n substances defined by a chemical image having a plurality of pixels, the apparatus comprising a processor to be used with a host computer, the processor programmed with instructions to: (i) provide a spectrum for each of the n substances in the mixture; (ii) obtain a spectrum for one of the plurality of pixels; (iii) calculate a plurality of estimated concentrations of each substance in the mixture as a function of the spectrum for each substance and the spectrum for the pixel; (iv) calculate a deviation value for each of the plurality of estimated concentrations as a function of the spectrum of each of the n substances; and (v) select the estimated concentration with the lowest deviation value as a most-likely concentration of each substance in the mixture.

In another embodiment, the disclosure relates to a system for determining percentage distribution of a substance in a mixture of substances defined by a chemical image of a plurality of pixels, the system comprising: a database for storing spectra of each substance in the mixture; and a processor in communication with the database, the processor programmed with instructions to: (i) retrieve a spectrum for each of the n substances in the mixture; (ii) obtain a spectrum for one of the plurality of pixels; (iii) calculate a plurality of estimated concentrations of each substance in the mixture as a function of the pixel spectrum and the spectrum for each substance; (iv) calculate a deviation value corresponding to each of the plurality of estimated concentrations; and (v) select a most-likely concentration from among the deviations values to represent the percentage distribution of each substance in the mixture.

In another embodiment, the disclosure relates to a system for determining percentage distribution of a substance in a mixture of substances defined by a chemical image of a plurality of pixels, the system comprising: a database for storing a spectrum for each substance in the mixture and a processor in communication with the database, the processor programmed with instructions to: (a) provide a spectrum for each of the n substances in the mixture; (b) obtain a spectrum for one of the plurality of pixels; (c) calculate an estimated concentration for each substance in the mixture as a function of the pixel spectrum and substance spectrum; (d) calculate an estimated pure spectra for each substance as a function of the estimated concentration for each substance and the pixel spectrum; (e) calculate a deviation value as a function of the estimated pure spectrum and the pure spectrum; (f) repeat steps (c)-(e) $2^n-1$ times with different combination of n substances to determine m deviation values; and (g) select a most-likely concentration corresponding from among m deviation values.

In still another embodiment, the disclosure relates to a machine-readable medium having stored thereon a plurality of executable instructions to be executed by a processor to implement a method for determining concentration of a substance in a mixture of n substances defined by a chemical image having a plurality of pixels, the method comprising: (a) providing a spectrum for each of the n substances in the mixture; (b) obtaining a spectrum for one of the plurality of pixels; (c) calculating an estimated concentration for each substance in the mixture as a function of the pixel spectrum and the substance spectrum; (d) calculating an estimated pure spectrum for each substance as a function of the estimated concentration for each substance and the pixel spectrum; (e) calculating a deviation value from the estimated pure spectrum and the pure spectrum; (f) repeating steps (c)-(e) $2^n-1$ times with different selections of n substances to determine m deviation values; and (g) selecting a most-likely concentration corresponding to the lowest among the m deviation values.

DETAILED DESCRIPTION

Figure 1A:
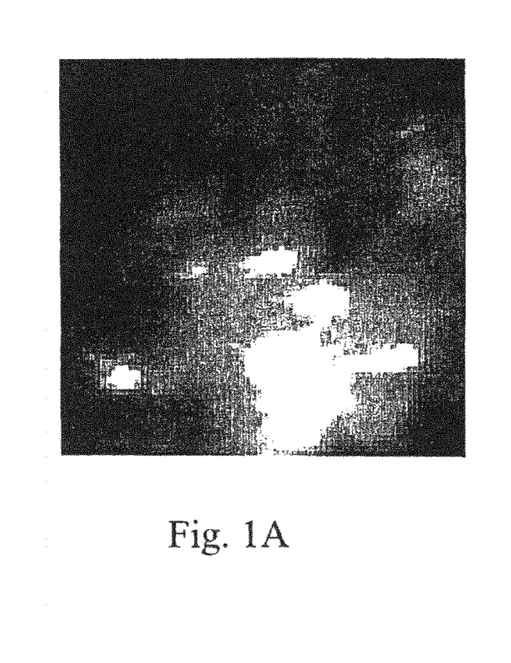
FIG. 1A is an exemplary chemical image for a mixture of three substances.
Figure 1B:
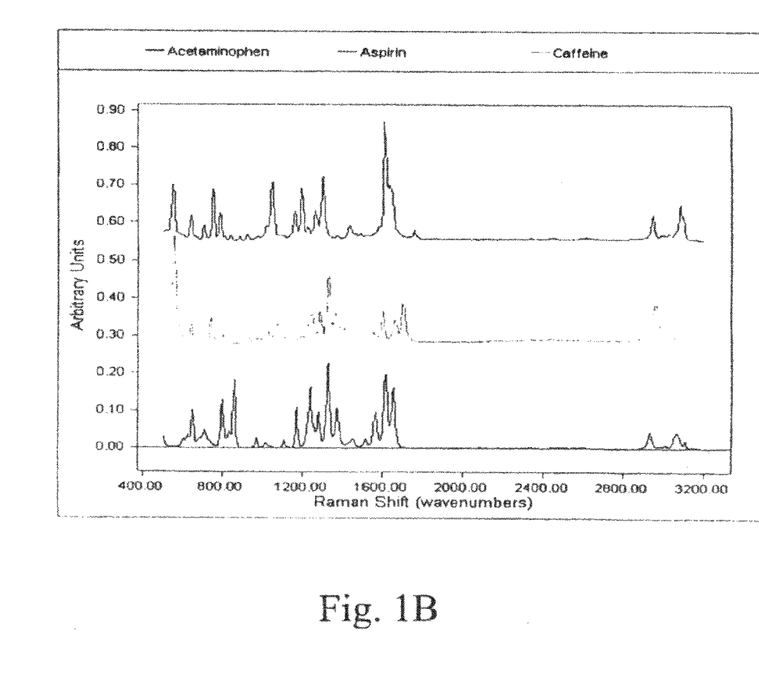
FIG. 1B is the spectrum for each of the substances in FIG. 1A.

FIG. 1A is an exemplary chemical image for a mixture of three substances. Particularly, FIG. 1A is a chemical image of a mixture containing aspirin, caffeine and acetaminophen. The chemical image can be obtained by point-mapping or through wide-field illumination of the sample. FIG. 1B is the spectrum for each of the substances in FIG. 1A. As can be seen from FIG. 1A, a chemical image is a 3-D representation of the sample under study. A chemical image is conventionally obtained by compiling a number of frames, with each pixel depicting a spectrum collected from the sample at different wavelengths. In other words, the chemical image is formed from a compilation of many spectra at different wavelengths. The chemical image is conventionally displayed on a screen display having a multitude of pixels. Hence, each pixel represents a small segment or a portion of the sample.

Figure 2:
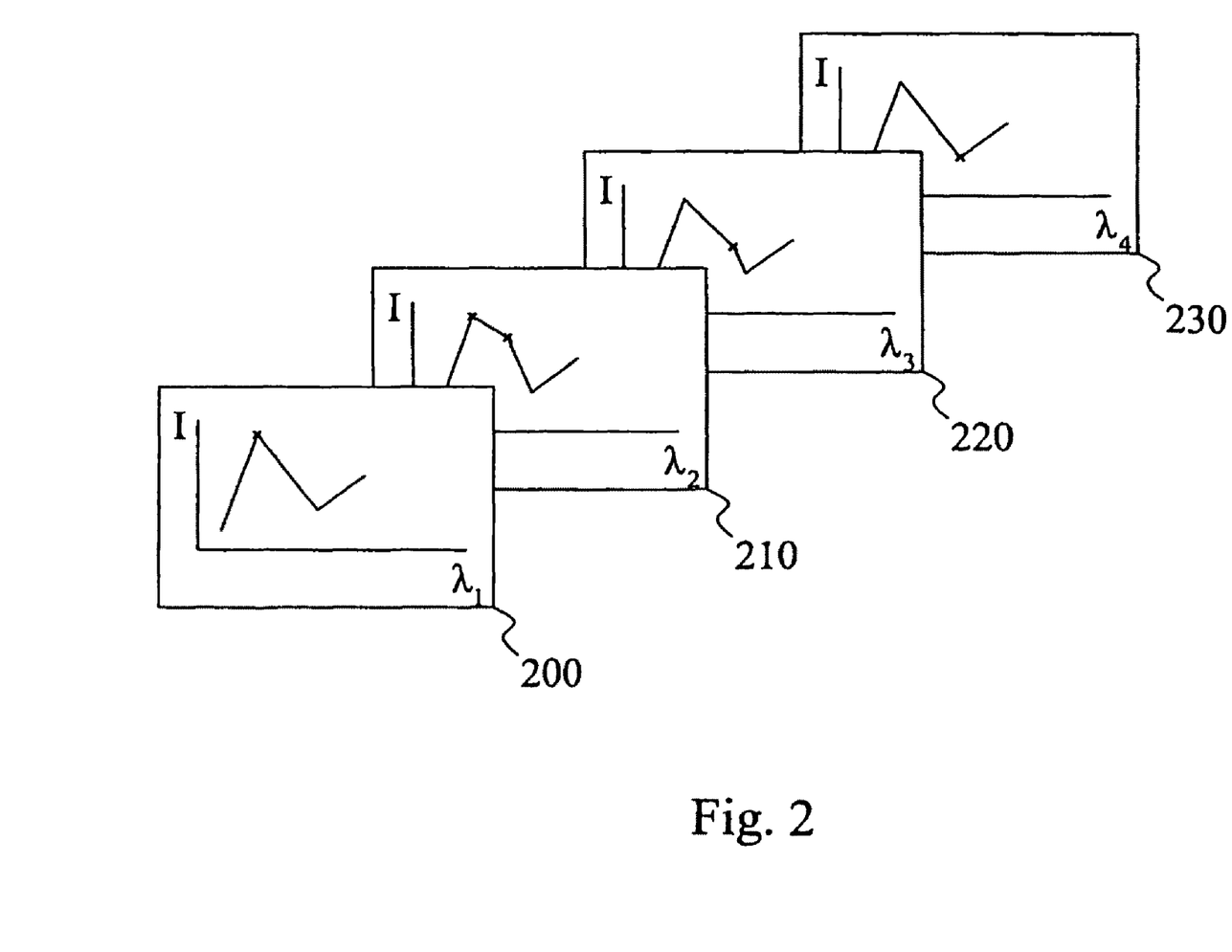
FIG. 2 schematically shows an exemplary spectrum for a pixel.

Since a chemical image is compiled from several frames having a plurality of spectra, it follows that a pixel can be deconstructed into a plurality of frames where each frame of the pixel denotes a relationship between intensity and wavelength (or wave-number). FIG. 2 schematically shows an exemplary spectrum for a pixel. As can be seen from FIG. 2, the spectral representation of a pixel shows the intensity and wave-number relationship for the pixel at wave-numbers common to all spectra of the sample.

Figure 3A:
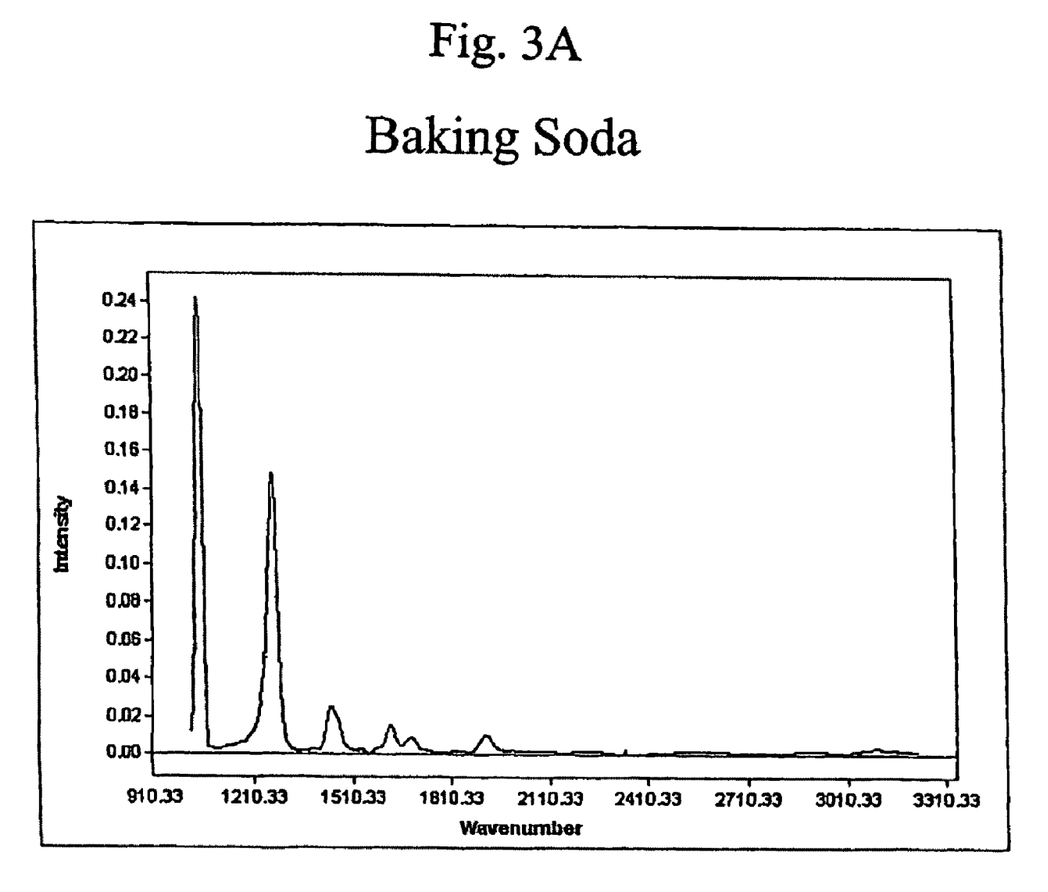
FIG. 3A is a spectral representation of baking soda.
Figure 3B:
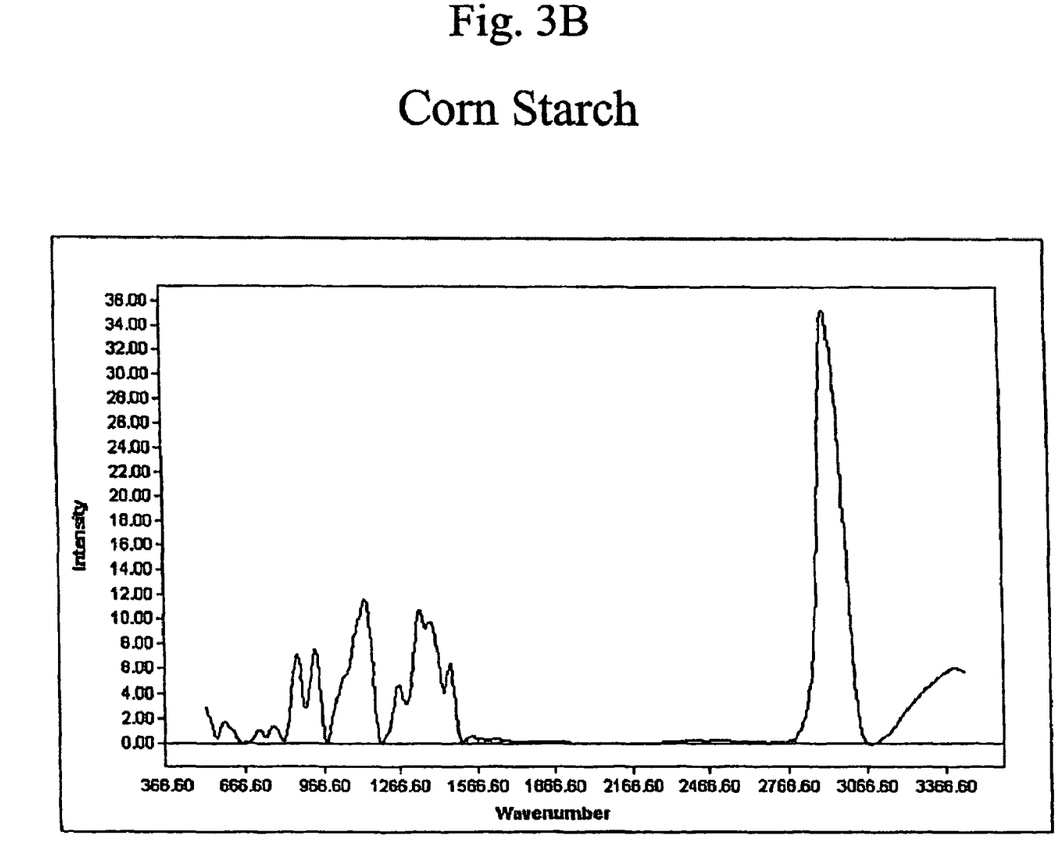
FIG. 3B is a spectral representation of corn starch.
Figure 3C:
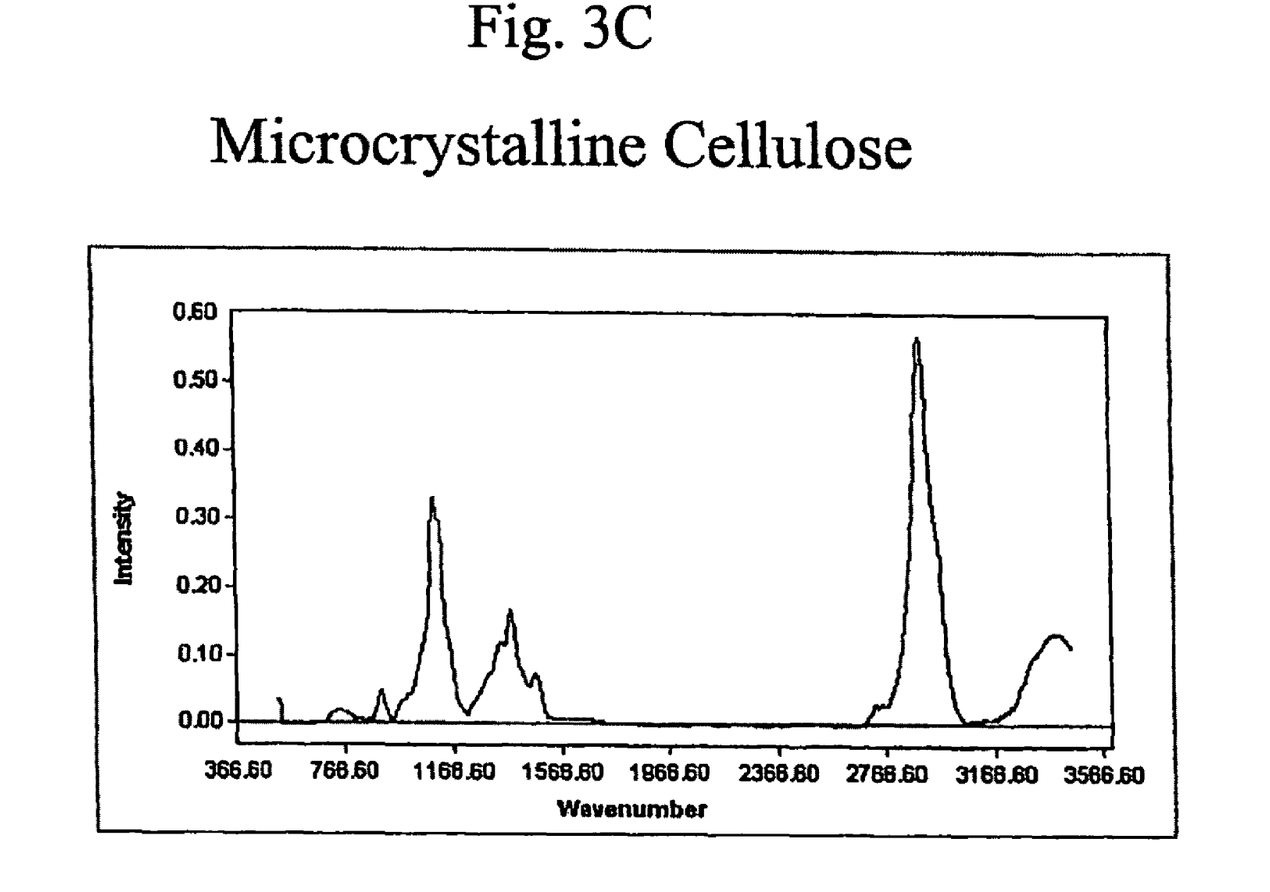
FIG. 3C is a spectral representation of microcrystalline cellulose.
Figure 3D:
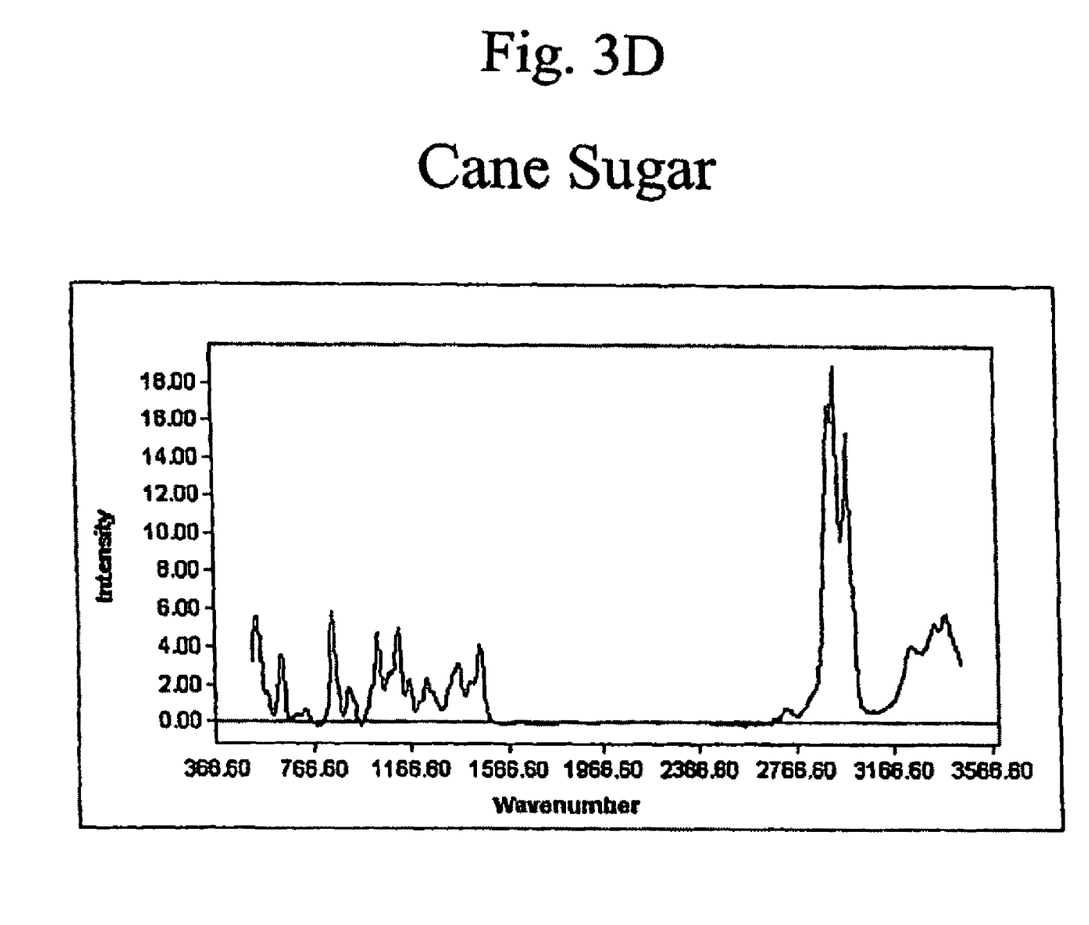
FIG. 3D is a spectral representation of cane sugar.

FIGS. 3A-3D are spectral representations of common substances which exist as white powder. Specifically, FIG. 3A is the spectral representation of backing soda; FIG. 3B is the spectral representation of corn starch; FIG. 3C is the spectral representation of microcrystalline cellulose and FIG. 3D is the spectral representation of cane sugar. The spectra of other substances are readily available and can be compiled in a library spectra. A mixture of the baking soda, corn starch, microcrystalline cellulose and cane sugar will be a white powder of roughly a similar consistency. It would be nearly impossible to identify the constituents by visual inspection.

Figure 4:
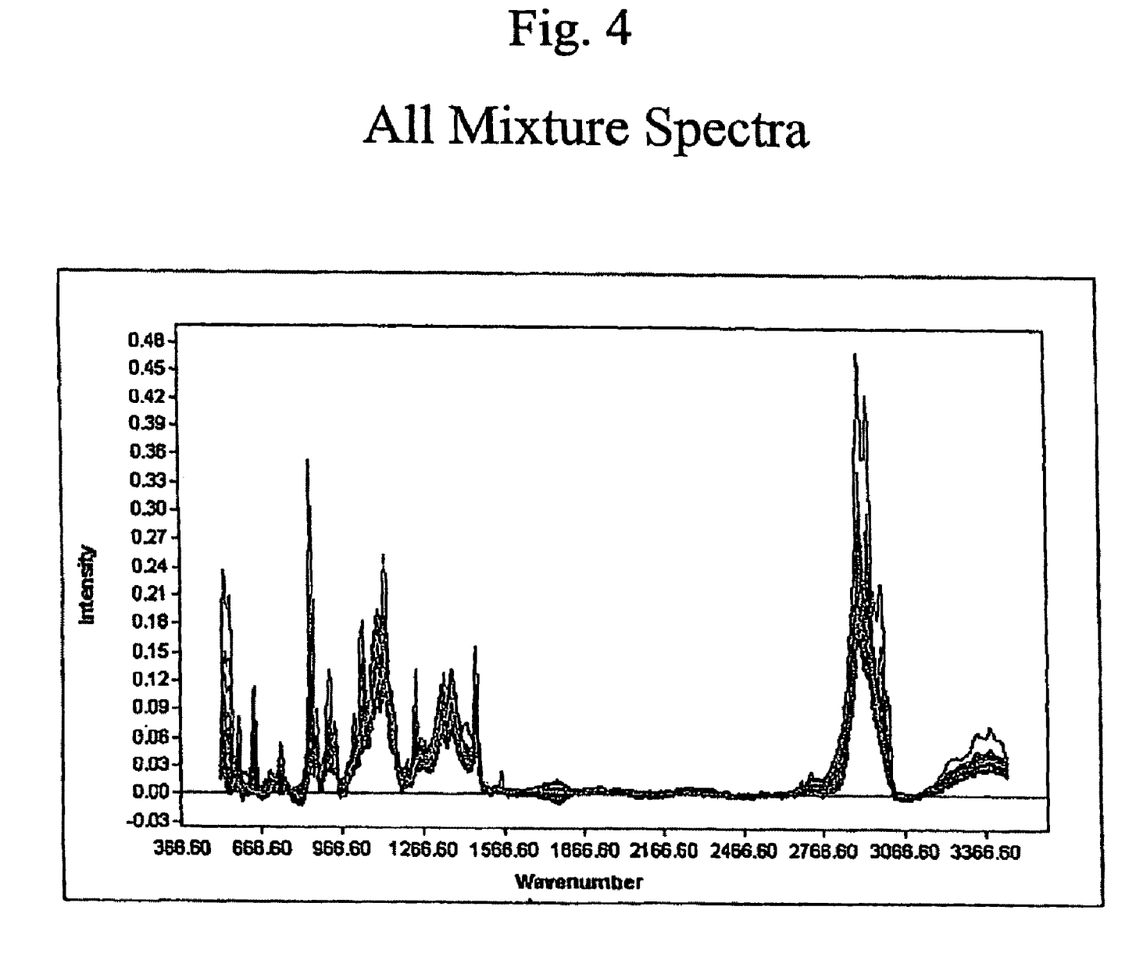
FIG. 4 is a spectral representation of a physical mixture containing several substances.

FIG. 4 is a spectral representation of a physical mixture containing several substances. The mixture spectra can be collected using various spectroscopical techniques, including infrared, Raman, Fluorescence and near infrared techniques. The mixture spectra, as well as the library spectra, should be corrected to remove all signals and information that are not due to the chemical compositions of the mixture sample and known elements/material. Such anomalies include various instrumental effects, such as the transmission of optical elements, the detector's responsiveness, and any other non-desired sample effect due to the instrument utilized for collecting the spectra. The mixture spectra and the library spectra may be corrected to remove instrumental artifacts using any of a variety of known correction methods. However, it is noted that the uncorrected spectra may also be used without departing from the principles disclosed herein. Thus, an optional step according to an embodiment of the disclosure is to remove instrument-dependent error from the spectra. This step can be implemented by using the transfer function of the instrument.

Figure 5:
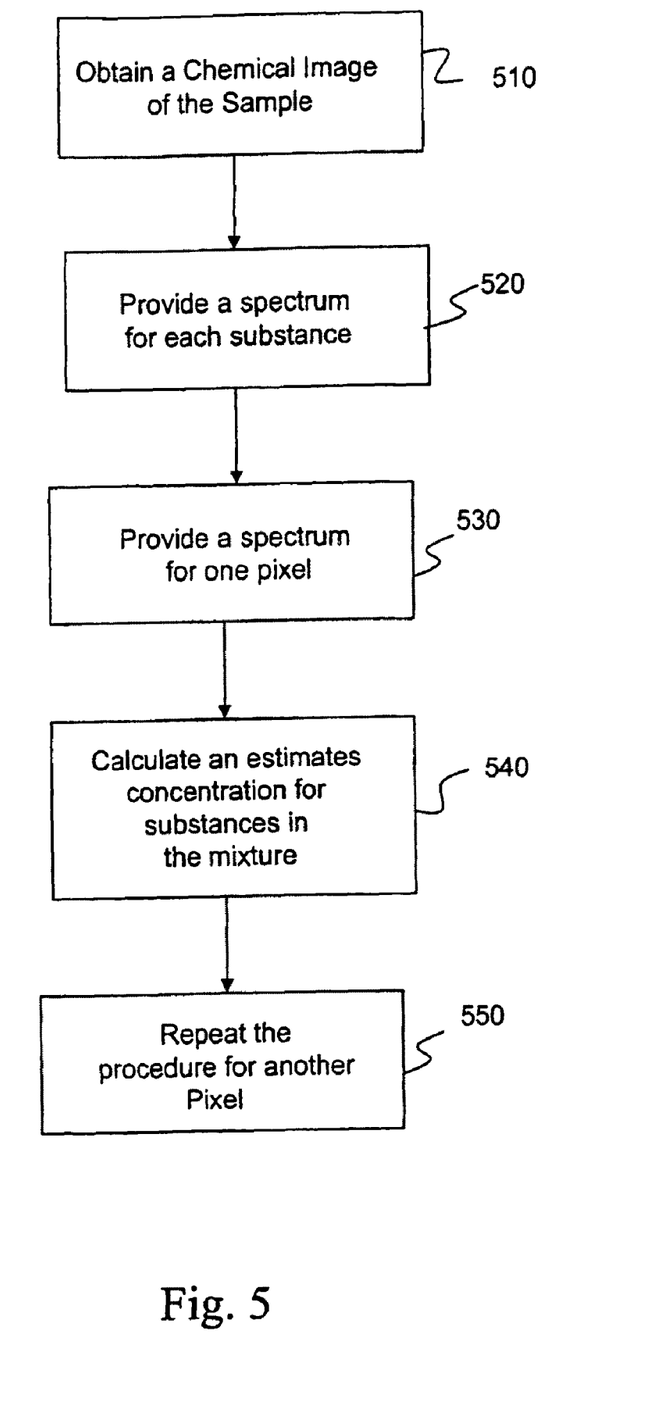
FIG. 5 is a flow-chart according to one embodiment of the disclosure.

FIG. 5 is a flow-chart according to one embodiment of the disclosure. Referring to FIG. 5, in step 510 a chemical image of the sample is obtained. The sample can be a physical mixture of two or more substances. Each substance may be an essentially pure element or a combination of two or more such elements. The chemical image can be an image of the entire sample or an image of a portion of the sample. If the chemical image depicts only a portion of the sample, it may be desirable to provide multiple chemical images in order to better gauge the substances' distribution throughout the sample.

In step 520 a spectrum for each substance in the mixture is provided. The pure spectrum can be provided by an operator with apriori knowledge of possible constituents of the mixture. Alternatively, spectra from different candidates can be used to determine its potential presence in the mixture. As stated, the spectra of various known substances and compounds can be stored in an electronic database or a library. Such database can be co-located with an apparatus according to an embodiment of the disclosure. Alternatively, the database can be at a different location and configured for access by the apparatus. For example, a wireless communication system can be used to access the database and retrieve pertinent spectral information. The spectrum for each substance can be a correlation of the Raman intensity and wave-number.

In step 530 the spectrum for a single pixel is provided. The single-pixel spectrum can be obtained directly from the chemical image (see step 510). As discussed with respect to FIG. 2, a spectrum for the pixel can be prepared by compiling the intensity/wave-number (interchangeably, intensity/wavelength) relationship from the various frames that form the pixel. Other methods can also be used without departing from the principles disclosed herein.

Once the pixel spectra and pure substance spectra are provided, the concentration of the various substances in the mixture can be calculated (see step 540). In one embodiment of the disclosure, the implementation of this step is an iterative process that can result in the most-likely estimate for each substance's concentration. According to another embodiment the concentration is calculated as a non-iterative estimation.

According to one embodiment of the disclosure the concentration of the various substances in the mixture can be calculated using equation (1) as follows:

$$\text{Data} = (\text{Estimated Concentration} \times \text{Substance Spectra}) + \text{Error term} \quad (1)$$

The error term in equation (1) is intended to identify and remove the spectral error associated with optical instruments as discussed above. One of ordinary skill in the art can readily identify one or more transfer-functions for the optical instruments used in chemical imaging of the sample. With the Error term removed, equation (1) is reduced to:

$$\text{Data} = \text{Estimated Concentration} \times \text{Substance Spectra} \quad (2)$$

The Data term of equation (2) represents the pixel's spectral information. The Data term can be presented as a 1×N matrix. The Substance spectrum represents the pure spectra for each substance. As stated, the pure spectra can be stored in a database library and be readily accessible. The Substance spectrum can also be represented as a matrix. Given values for the Data term and the Substance spectra, equation (2) can be solved to determine an estimated concentration for each substance represented in the pixel. As will be discussed in relation to FIG. 6, the process of determining estimated concentration can be optionally repeated to provide various values of estimated concentration. According to one embodiment, the various concentration estimates can be evaluated for accuracy and ranked accordingly. In one embodiment, the estimated concentration ranked highest is selected as the estimated concentration.

In step 550 of FIG. 5, the processes of steps 520-540 are repeated for one or more pixels from the chemical image. The process steps disclosed in FIG. 5 can be repeated for only one, a few or all of the pixels in the chemical image. If the chemical image (step 510) is an image of the entire sample, then implementing the exemplary process of FIG. 5 can provide the concentration distribution for the entire sample. On the other hand, if the chemical image only depicts a portion of the sample, then it may be desirable to repeat the exemplary process of FIG. 5 for different pixels depicting alternative portions of the samples.

Figure 6:
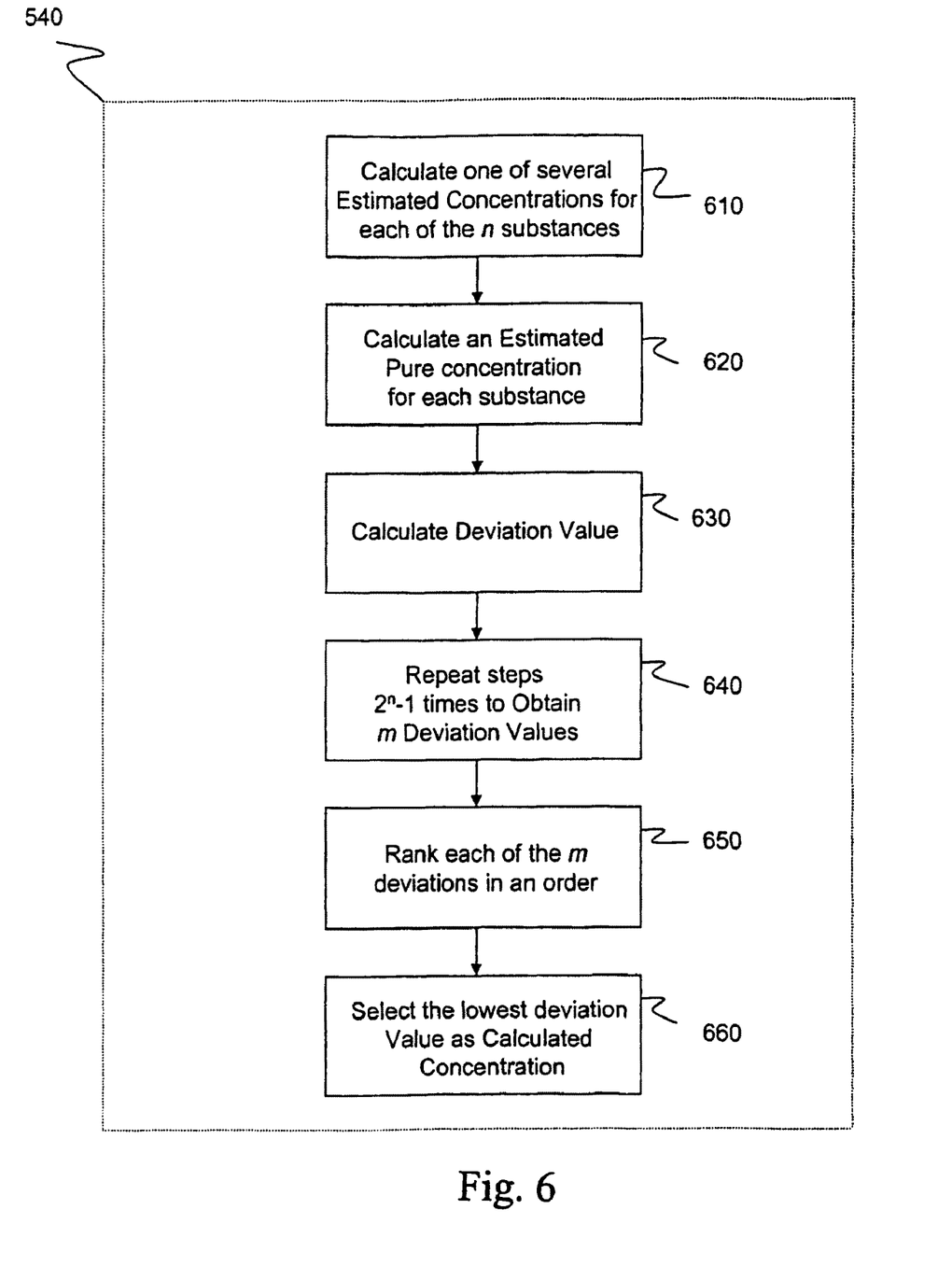
FIG. 6 is a flow-chart according to another embodiment of the disclosure.

FIG. 6 is a flow-chart according to another embodiment of the disclosure. More specifically, FIG. 6 shows a method for ranking the accuracy of estimated concentration according to one embodiment of the disclosure (see step 540 in FIG. 5). Referring to FIG. 6, step 610 is directed to calculating one of several Estimated Concentrations for each of the n substances in the mixture. For a mixture of n substances, there can be $2^n - 1$ different combination substances. By way of example, a mixture of caffeine, aspirin and acetaminophen can have 7 (i.e., $2^3 - 1$) different combinations of elements. Thus, in an exemplary embodiment, steps 610-640 are repeated seven times for such a mixture. The Estimated Concentrations can be calculated, for example, by using equations (1) or (2).

Once a first set of Estimated Concentration values are obtained in step 610, these values are used to determine an Estimated Pure concentration. Equation (2) can be used to aid this calculation. Accordingly, the Data component of the equation would be the same as before (i.e., a matrix defining pixel intensity/wave-number relationship) and the values obtained in step 610 can be used for Estimated Concentration portion of the equation to calculate an Estimated Pure Concentration. Since the equation operates in matrixes, the Estimated Pure Concentration would include an estimated concentration for each of the substances in the mixture.

In step 630 the Estimated Pure Concentrations and the known Pure Concentrations (e.g., from spectral library) are compared to arrive at a deviation value. The deviation value may depict the percentage deviation between the Estimated and the known values. The deviation value can be stored in a memory table for future reference. In step 640, the exemplary embodiment calls for repeating the process steps 610-630 for a number of times ($2^n - 1$) to compile m deviation values ($m = 2^n - 1$). It should be noted that sub-routine of step 640 is exemplary and non-limiting. Thus, these steps can be repeated 2, 3 or n times.

Once the several Estimated Concentration values have been calculated and a corresponding deviation value has been defined, then the deviation values can be ranked in an order to identify the most-likely Estimated Concentration (step 660). The most-likely concentration would indicate the most probable concentration of each substance in the mixture at the location represented by the pixel. To determine the most-likely concentration across the entire image, the process can be repeated for all other pixels in the chemical image.

The process steps disclosed herein can be reduced to sub-routines of a software program. Thus, an embodiment of the disclosure relates to a software configured to use a chemical image to identify possible concentrations of various substances in a mixture. In another embodiment, the process steps can be programmed to a processor adapted to implement these steps. Such processor can be used with a host computer and other peripherals to implement the various embodiments. In one such exemplary embodiment, a processor can be programmed to implement steps identified in FIGS. 5 and 6. The processor can be configured to receive one or more chemical images and retrieve the spectra for each pure component from a spectral library stored in a database.

In still another embodiment, the process steps can be implemented on a bench-top or a portable device. The device can be configured to obtain a chemical image directly from the sample and implement the disclosed embodiments to determine the concentration for each substance in the mixture.

While the disclosure has been described using illustrative embodiments and specific algorithms provided herein, it should be understood that the principles of the disclosure are not limited thereto and may include modification thereto and permutations thereof.

What is claimed is:

1. A method for determining concentration of a substance in a mixture of n substances defined by a chemical image having a plurality of pixels, the method comprising; using at least one processor for:

(a) providing a spectrum for each of the n substances in the mixture;

(b) obtaining a spectrum for one of the plurality of pixels, the spectrum defining the pixel as a function of intensity and wavelength;
(c) calculating an estimated concentration for each substance in the mixture as a function of the spectrum for each substance and the pixel spectrum;
(d) calculating an estimated pure spectrum for each substance as a function of the estimated concentration for each substance and the pixel spectrum;
(e) calculating a deviation value as a function of the estimated pure spectrum and the spectrum provided in step (b);
(f) repeating steps (c)-(e) $2n-1$ times with different combinations of n substances to determine m deviation values; and
(g) selecting the lowest deviation value from among m deviation values as the most-likely concentration for each substance in the mixture.

2. The method of claim 1, further comprising repeating steps (a)-(g) for at least one other pixel in the image.

3. The method of claim 1, wherein the substance is an essentially pure element.

4. The method of claim 1, wherein the substance is a combination of at least two elements.

5. The method of claim 1, wherein the step of providing a spectrum for each of the n substances in the mixture further comprises defining each substance as a function of intensity and wavelength.

6. The method of claim 1, wherein the step of providing a spectrum for each of the n substances in the mixture further comprises defining each substance as a function of intensity and wave-number.

7. The method of claim 1, wherein the step of obtaining a spectrum for one of the plurality of pixels further comprises identifying a plurality of frames associated with each pixel.

8. The method of claim 7, further comprising defining a relationship between intensity and wave-number for each frame.

9. A method for determining concentration of a substance in a mixture of n substances defined by a chemical image having a plurality of pixels, the method comprising; using at least one processor for:
(i) providing a spectrum for each of the n substances in the mixture;
(ii) obtaining a spectrum for one of the plurality of pixels; the spectrum defining the pixel as a function of intensity and wavelength;
(iii) calculating a plurality of estimated concentrations for each substance in the mixture as a function of the spectrum for each substance and the pixel spectrum;
(iv) calculating a deviation value for each of the plurality of estimated concentrations as a function of the estimated concentration and the spectrum for each of the n substances;
(v) calculating $2n-1$ combinations of possible concentrations to determine m estimated concentrations; and
(vi) selecting the estimated concentration with the lowest deviation value as a most-likely concentration of each substance in the mixture.

10. The method of claim 9, further comprising: (vi) repeating steps (iii)-(v) for at least one other pixel in the image.

11. The method of claim 9, wherein the substance is an essentially pure element.

12. The method of claim 9, wherein the substance is a combination of at least two elements.

13. The method of claim 9, wherein the step of providing a spectrum for each of the n substances in the mixture further comprises defining each substance as a function of intensity and wavelength.

14. The method of claim 9, wherein the step of providing a spectrum for each of the n substances in the mixture further comprises defining each substance as a function of intensity and wave-number.

15. The method of claim 9, wherein the step of obtaining a spectrum for one of the plurality of pixels further comprises identifying a plurality of frames associated with each pixel.

16. The method of claim 15, further comprising defining a relationship between intensity and one of wavelength or wave-number for the frame.

17. The method of claim 9, wherein the step of calculating a deviation factor further comprises:
(a) using the estimated concentration to calculate an estimated spectrum for each of the n substances in the mixture; and
(b) comparing the estimated spectrum for each of the n substances in the mixture with the corresponding actual spectrum for each substance as defined in step (i) to determine the deviation value.

18. The method of claim 17 further comprising repeating steps (a) and (b) for $2n-1$ times to determine m deviation values.

19. An apparatus for determining concentration of a substance in a mixture of n substances defined by a chemical image having a plurality of pixels, the apparatus comprising a processor to be used with a host computer, the processor programmed with instructions to:
(i) provide a spectrum for each of the n substances in the mixture;
(ii) obtain a spectrum for one of the plurality of pixels; the spectrum defining the pixel as a function of intensity and wavelength;
(iii) calculate a plurality of estimated concentrations of each substance in the mixture as a function of the spectrum for each substance and the spectrum for the pixel;
(iv) calculate a deviation value for each of the plurality of estimated concentrations as a function of the spectrum of each of the n substances;
(v) calculate $2n-1$ combinations of possible concentrations to determine m estimated concentrations; and
(vi) select the estimated concentration with the lowest deviation value as a most-likely concentration of each substance in the mixture.

20. The apparatus of claim 19, wherein the processor is further programmed with instructions to: (vi) repeat steps (iii)-(v) for at least one other pixel in the image.

21. The apparatus of claim 19, wherein the substance is an essentially pure element.

22. The apparatus of claim 19, wherein the substance is a combination of at least two elements.

23. The apparatus of claim 19, wherein the instruction to provide a spectrum for each of the n substances in the mixture further comprises defining each substance as a function of intensity and wavelength.

24. The apparatus of claim 19, wherein the instruction to provide a spectrum for each of the n substances in the mixture further comprises defining each substance as a function of intensity and wave-number.

25. The apparatus of claim 19, wherein the instruction to obtain a spectrum for one of the plurality of pixels further comprises identifying a plurality of frames associated with each pixel.

26. The apparatus of claim 25, further comprising defining a relationship between intensity and one of wavelength or wave-number for the frame.

27. The apparatus of claim 19, wherein the instruction to calculate a deviation value further comprises:
(a) using the estimated concentration to calculate an estimated spectrum for each of the n substances in the mixture; and
(b) comparing the estimated spectrum for each of the n substances in the mixture with the corresponding actual spectrum for each substance as defined in step (i) to determine the deviation value.

28. The apparatus of claim 27, further comprising repeating steps (a), (b) $2^n-1$ times to determine m deviation values.

29. A system for determining percentage distribution of a substance in a mixture of substances defined by a chemical image of a plurality of pixels, the system comprising:
a database for storing spectra of each substance in the mixture; and a processor in communication with the database, the processor programmed with instructions to:
(i) retrieve a spectrum for each of the n substances in the mixture;
(ii) obtain a spectrum for one of the plurality of pixels; the spectrum defining the pixel as a function of intensity and wavelength;
(iii) calculate a plurality of estimated concentrations of each substance in the mixture as a function of the pixel spectrum and the spectrum for each substance;
(iv) calculate a deviation value corresponding to each of the plurality of estimated concentrations;
(v) calculate $2n-1$ combinations of possible concentrations to determine m estimated concentrations; and
(vi) select the estimated concentration with the lowest deviation value as a most-likely concentration of each substance in the mixture.

30. The system of claim 29, wherein the processor is further programmed with instructions to: (vi) repeat steps (iii)-(v) for at least one other pixel in the image.

31. The system of claim 29, wherein the substance is an essentially pure element.

32. The system of claim 29, wherein the substance is a combination of at least two elements.

33. The system of claim 29, wherein the instruction to provide a spectrum for each of the n substances in the mixture further comprises defining each substance as a function of intensity and wavelength.

34. The system of claim 29, wherein the instruction to provide a spectrum for each of the n substances in the mixture further comprises defining each substance as a function of intensity and wave-number.

35. The system of claim 29, wherein the instruction to obtain a spectrum for one of the plurality of pixels further comprises identifying a plurality of frames associated with each pixel.

36. The system of claim 35, further comprising defining a relationship between intensity and one of wavelength or wave-number for the frame.

37. The system of claim 29, wherein the instruction to calculate a deviation value further comprises:
(a) using the estimated concentration to calculate an estimated spectrum for each of the n substances in the mixture; and
(b) comparing the estimated spectrum for each of the n substances in the mixture with the actual spectrum for each substance as defined in step (i) to determine the deviation value.

38. The system of claim 37, further comprising repeating steps (a), (b) $2^n-1$ times to determine m deviation values.

39. A system for determining percentage distribution of a substance in a mixture of substances defined by a chemical image of a plurality of pixels, the system comprising:
a database for storing a spectrum for each substance in the mixture and a processor in communication with the database, the processor programmed with instructions to:
(a) provide a spectrum for each of the n substances in the mixture;
(b) obtain a spectrum for one of the plurality of pixels;
(c) calculate an estimated concentration for each substance in the mixture as a function of the pixel spectrum and substance spectrum;
(d) calculate an estimated pure spectrum for each substance as a function of the estimated concentration for each substance and the pixel spectrum;
(e) calculate a deviation value as a function of the estimated pure spectrum and the pure spectrum;
(f) repeat steps (c)-(e) $2^n-1$ times with different combination of n substances to determine m deviation values; and
(g) select a most-likely concentration corresponding from among m deviation values.

40. The system of claim 39, further comprising repeating steps (a)-(g) for at least one other pixel in the image.

41. The system of claim 39, wherein the substance is an essentially pure element.

42. The system of claim 39, wherein the substance is a combination of at least two elements.

43. The system of claim 39, wherein the instruction to provide a spectrum for each of the n substances in the mixture further comprises defining each substance as a function of intensity and wavelength.

44. The system of claim 39, wherein the instruction to provide a spectrum for each of the n substances in the mixture further comprises defining each substance as a function of intensity and wave-number.

45. The system of claim 39, wherein the instruction to obtain a spectrum for one of the plurality of pixels further comprises identifying a plurality of frames associated with each pixel.

46. The system of claim 45, further comprising defining a relationship between intensity and wave-length for each frame.

47. A non-transitory machine-readable medium having stored thereon a plurality of executable instructions to be executed by a processor to implement a method for determining concentration of a substance in a mixture of n substances defined by a chemical image having a plurality of pixels, the method comprising:
(a) providing a spectrum for each of the n substances in the mixture;
(b) obtaining a spectrum for one of the plurality of pixels; the spectrum defining the pixel as a function of intensity and wavelength;
(c) calculating an estimated concentration for each substance in the mixture as a function of the pixel spectrum and the substance spectrum;
(d) calculating an estimated pure spectrum for each substance as a function of the estimated concentration for each substance and the pixel spectrum;
(e) calculating a deviation value from the estimated pure spectrum and the pure spectrum;

(f) repeating steps (c)-(e) 2n−1 times with different selections of n substances to determine m deviation values; and
(g) selecting a most-likely concentration corresponding to the lowest among the m deviation values for each substance in the mixture.

48. A machine-readable medium of claim 47, further comprising repeating steps (a)-(g) for at least one other pixel in the image.

* * * * *